United States Patent

Andres et al.

Patent Number: 5,352,787
Date of Patent: Oct. 4, 1994

[54] PROCESS FOR THE PREPARATION OF 5-(TRIFLUOROMETHYL)-URACIL, AND THE NOVEL COMPOUNDS 2,4-DICHLORO-5-TRICHLOROMETHYL-PYRIMIDINE AND 2,4-DIFLUORO-5-TRIFLUOROMETHYL-PYRIMIDINE

[75] Inventors: Peter Andres, Leichlingen; Albrecht Marhold, Leverkusen, both of Fed. Rep. of Germany

[73] Assignee: Bayer Aktiengesellschaft, Leverkusen, Fed. Rep. of Germany

[21] Appl. No.: 86,696

[22] Filed: Jul. 2, 1993

[30] Foreign Application Priority Data

Jul. 9, 1992 [DE] Fed. Rep. of Germany ....... 4222518

[51] Int. Cl.$^5$ ............................................. C07D 239/02
[52] U.S. Cl. .................................. 544/309; 544/313; 544/334; 204/157.72
[58] Field of Search ............ 544/309, 313, 334; 204/157.72

[56] References Cited

U.S. PATENT DOCUMENTS

| | | | |
|---|---|---|---|
| 2,937,171 | 5/1960 | Smith | 544/334 |
| 3,201,387 | 8/1965 | Heidelberger | 544/309 |
| 3,314,955 | 4/1967 | Boudakian et al. | 544/334 |
| 3,324,126 | 6/1967 | Mertes et al. | 544/314 |
| 3,485,839 | 12/1969 | Fuller | 544/334 |
| 3,580,913 | 5/1971 | Lutz | 544/309 |
| 3,694,444 | 9/1972 | Klauke et al. | 544/334 |
| 3,869,457 | 3/1975 | Lutz | 544/309 |
| 4,137,412 | 1/1979 | Braden et al. | 544/334 |
| 4,299,961 | 11/1981 | De Pasquale et al. | 544/334 |
| 4,659,827 | 4/1987 | Herd et al. | 544/334 |
| 4,668,788 | 5/1987 | Beitzke et al. | 544/334 |

FOREIGN PATENT DOCUMENTS 8174372 10/1983 Japan .

OTHER PUBLICATIONS

March, Advanced Org. Chem. 3rd Edition, (1985) pp. 618–620.
Bernd et al, Chem. Abst. 104(15): 129919b (1985).
Chem. Abst. 101(25): 230565w (1984).
Banks et al, Chem. Abst. 73(5): 25402c (1970).
*J. Pharm. Sci.*, 52 (1963); "Use of Sulfur Tetrafluoride in Syntheses of Potential Anticancer Agents", Peter P. Mertes and Souheil E. Saheb, pp. 508 and 509.

*Primary Examiner*—Cecilia Tsang
*Attorney, Agent, or Firm*—Sprung Horn Kramer & Woods

[57] ABSTRACT

5-Trifluoromethyl-uracil is obtained by chlorinating thymine under mild conditions, further chlorinating the resulting 2,4-dichloro-5-methyl-pyrimidine under drastic conditions to give 2,4-dichloro-5-trichloromethyl-pyrimidine, reacting the latter with a fluorinating agent to give 2,4-fluorinated and/or -chlorinated 5-trifluoromethylpyrimidines and subjecting these to hydrolysis. The novel chemical compounds 2,4-dichloro-5-trichloromethylpyrimidine and 2,4-difluoro-5-trifluoromethylpyrimidine are obtained in the course of this process.

6 Claims, No Drawings

PROCESS FOR THE PREPARATION OF 5-(TRIFLUOROMETHYL)-URACIL, AND THE NOVEL COMPOUNDS 2,4-DICHLORO-5-TRICHLOROMETHYL-PYRIMIDINE AND 2,4-DIFLUORO-5-TRIFLUOROMETHYL-PYRIMIDINE 5-(Trifluoromethyl)-uracil is an important intermediate for the preparation of trifluridine (=5'-trifluoromethyl-2'-deoxyuridine=trifluorothymidine=TFT), a known antiviral active ingredient (see Römpp's Chemie-Lexikon, 8th edition, volume 6, p. 4350 (1988)).

It is known that 5-(trifluoromethyl)-uracil can be obtained by reacting uracil-5-carboxylic acid with sulphur tetrafluoride [see J. Pharm. Sci. 52, 508, (1963)]. In this reaction, sulphur tetrafluoride, which is highly poisonous, is required in large excess and uracil-5-carboxylic acid, which is not readily available, is required as the starting material.

A process for the preparation of 5-(trifluoromethyl)uracil has now been found which is characterised in that
  a) thymine is chlorinated under mild conditions to give 2,4-dichloro-5-methyl-pyrimidine,
  b) this is further chlorinated under drastic conditions to give 2,4-dichloro-5-trichloromethyl-pyrimidine,
  c) this is reacted with a fluorinating agent to give 2,4-fluorinated and/or -chlorinated 5-trifluoro methylpyrimidines, and
  d) these are subjected to hydrolysis.

The present invention further relates to the novel chemical compound 2,4-dichloro-5-trichloromethyl-pyrimidine, which can be isolated after step b) has been carried out, and the novel chemical compound 2,4-difluoro-5-trifluoromethyl-pyrimidine, which can be isolated after step c) has been carried out.

The process according to the invention can be illustrated by the following reaction scheme:

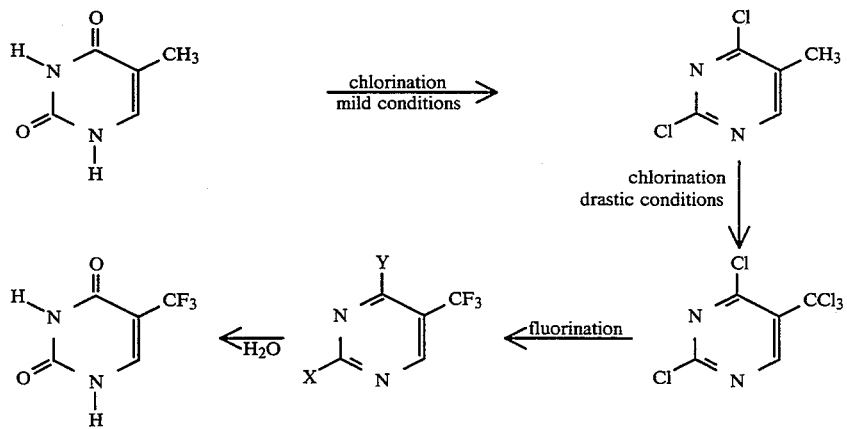

X and Y=chlorine or fluorine

The thymine (=5-methyl-uracil) required as the starting material is commercially available or can be prepared by the process described in J. Am. Chem. Soc. 68, 912 (1946).

Step a) of the process according to the invention can be carried out for example by reacting phosphorus oxychloride with thymine in the presence of a tertiary amine at 20° to 120° C. Based on one mol of thymine, it is possible to use for example 3 to 25 mol of phosphorus oxychloride and 0.1 to 1 mol of a tertiary amine, for example N,N-dimethylaniline. It is generally advantageous to bring these reactants together at room temperature and to complete the reaction at temperatures of between 30° C. and the reflux temperature, preferably with the phosphorus oxychloride boiling under reflux.

The resulting reaction mixture can be worked up for example by first cooling it, removing the excess phosphorus oxychloride, e.g. by vacuum distillation, then stirring the residue with water and extracting it with an inert organic solvent and isolating the 2,4-dichloro-5-methyl-pyrimidine from the organic phase. After separation of the excess phosphorus oxychloride, 2,4-dichloro-5-methyl-pyrimidine can also be isolated by distillation. As a rule, the yield is in the range from 85 to 95%.

Step b) of the process according to the invention can be carried out for example by chlorinating 2,4-dichloro-5-methyl-pyrimidine at temperatures of 180° to 250° C. with elemental chlorine under UV irradiation and without adding a solvent. It is also possible to use sulphuryl chloride as the chlorinating agent and to add radical-forming agents, for example azoisobutyronitrile or peroxides, in addition to or instead of UV irradiation.

The chlorinating agent is conveniently introduced until gas chromatography shows that all the methyl hydrogen atoms present have been substituted by chlorine. The 2,4-dichloro-5-trichloromethyl-pyrimidine formed is a novel chemical compound and, if desired, can be purified by vacuum distillation. As a rule, the yield in this step is 85 to 95%.

Step c) of the process according to the invention can be carried out for example by reacting 2,4-dichloro-5-trichloromethyl-pyrimidine, optionally in the presence of a catalytic amount of antimony halides, with excess hydrogen fluoride under pressure at temperatures of 80° to 180° C. and relieving the pressure of the hydrogen chloride formed via a condenser equipped with a retention valve. If it is desired to obtain the novel chemical compound 2,4-difluoro-5-trifluoromethyl-pyrimidine with good yields and selectivities, it is possible to work with or without adding antimony halides. If mixtures of SbF$_3$ and SbCl$_5$ are used as the fluorinating agent, 2,4-chlorofluoro-and 2,4-dichloro-5-trifluoromethyl-pyrimidines are generally obtained in notable proportions in addition to 2,4-difluoro-5-trifluoromethyl-pyrimidine. This is of no particular importance for carrying out step d) of the process according to the invention because all these 2,4-dihalogeno-5-trifluoromethylpyrimidines can be converted to 5-trifluoromethyl-uracil by hydrolysis.

In general, mixtures containing 2,4-difluoro-, 2,4-chlorofluoro- and 2,4-dichloro-5-trifluoromethyl-pyrimidines are also obtained when the fluorinating agent used is only hydrogen fluoride in a less than stoichiometric amount.

In step c), it is possible to use, per mol of 2,4-dichloro-5-trichloromethyl-pyrimidine, for example 5 to 50 ml of antimony halides, preferably antimony pentachloride or mixtures of antimony trifluoride and antimony pentachloride, and, in addition to or instead of the antimony halides, 60 to 5000 ml of anhydrous hydrogen fluoride. When using approx. 60 ml of hydrogen fluoride per mol of pyrimidine, essentially only the trichloromethyl group is converted to a trifluoromethyl group. When using hydrogen fluoride e.g. in the range from approx. 65 to 100 ml per mol of pyrimidine, essentially one ring chlorine is additionally replaced with a fluorine atom, preferentially the one in the 4-position. When using more than 100 ml of hydrogen fluoride per mol of pyrimidine, essentially all the chlorine atoms present are replaced with fluorine atoms.

Preferred reaction temperatures are in the range from 120° to 170° C. The pressure can be for example 15 to 40 bar, preferably 20 to 30 bar. The working-up can be carried out e.g. by cooling, relieving the pressure, removing excess fluorinating agent and distilling the remaining residue. As a rule, the yield in this step is 70 to 90%.

Step d) of the process according to the invention can be carried out for example by reacting the 2,4-fluorinated and/or -chlorinated 5-trifluoromethyl-pyrimidines obtained in step c) with excess water at room temperature and/or elevated temperature. At temperatures in the range from 20° to 90° C., the saponification is often finished within a period of 5 to 24 hours. It is particularly advantageous to raise the temperature, e.g. briefly to the boiling point, at the end of the saponification reaction and then to filter the mixture hot. 5-Trifluoromethyl-uracil then crystallises out as the filtrate cools. It is possible to use e.g. 3 to 20 ml of water, based on 1 g of 2,4-fluorinated and/or -chlorinated 5-trifluoromethyl-pyrimidines. As a rule, the yield in this step is 85 to 95%.

It is advantageous to add potassium fluoride and/or sodium fluoride to the excess water, for example 0.5 to 2 mol of fluorides per mol of 2,4-dihalogenated 5-trifluoromethyl-pyrimidine.

The process according to the invention has a number of advantages: It can be carried out with readily available starting materials and simple reagents (e.g. $POCl_3$, $Cl_2$, HF and $H_2O$), it affords 5-trifluoromethyl-uracil in good yields and with little waste, and it can be carried out satisfactorily on the industrial scale.

It is surprising that the chlorination in step b) produces the chloromethyl compound in good yield and that practically no $CHCl_2$ and $CH_2Cl$ derivatives and practically no decomposition reactions are observed. It is further surprising that, in step c), up to 5 fluorine atoms can be introduced in one stage, said fluorine atoms then being found both on the aromatic ring and in the methyl side-chain. Finally, it is surprising that, in step d), only the ring fluorine or ring chlorine atoms are saponified and the $CF_3$ group remains intact. The latter might have been expected to undergo saponification as well to give a COOH group.

EXAMPLES

Example 1 (Preparation of 2,4-dichloro-5-methyl-pyrimidine)

48 g of dimethylaniline were slowly added dropwise to 3067 g of phosphorus oxychloride, with cooling, and the mixture was subsequently stirred for 5 minutes at 25° C. 252 g of thymine (=5-methyl-uracil) were then slowly added at 25° C. and the mixture was subsequently stirred under reflux for 20 hours. After cooling, excess phosphorus oxychloride still present was distilled off at 30° to 35° C. under a water-Jet vacuum and the remaining residue was distilled under vacuum to give 301 g (=92% of theory) of 2,4-dichloro-5-methyl-pyrimidine with a boiling point of 110° C. at a pressure of 16 mbar.

Example 2 (Preparation of 2,4-dichloro-5-trichloromethyl-pyrimidine)

257 g of 2,4-dichloro-5-methylpyrimidine were placed in a three-necked flask equipped with a reflux condenser, and chlorine was then introduced, under irradiation with a UV lamp and with the temperature increasing gradually up to 230° C., until gas chromatographic analysis showed that the $CCl_3$ product had been formed (approx. 35 hours). The 2,4-dichloro-5-trichloromethyl-pyrimidine obtained in this way was isolated by distillation. It had a boiling point of 80° to 82° C. at 0.08 mbar and a refractive index $n_D^{20}$ of 1.5903. It was obtained in a yield of 387 g (=92% of theory).

The $^1H$ NMR spectrum (200 MHz, $CDCl_3$) showed a characteristic signal at $\delta=9.3$ ppm. The mass spectrum (EI, 70 eV) showed characteristic bands at m/z=266 (6%), 231 (100%), 195 (10%), 161 (4%), 141 (26%) and 107 (18%).

Example 3 (Preparation of 2,4-difluoro-5-trifluoromethyl-pyrimidine)

400 g of 2,4-dichloro-5-trichloromethyl-pyrimidine, 30 ml of antimony pentachloride and 1700 ml of anhydrous hydrofluoric acid were placed in a stainless steel stirred autoclave and stirred under nitrogen for 4 hours at 150° C. and a pressure of 30 bar. The pressure of the hydrogen chloride formed was relieved continuously via a condenser. When the evolution of hydrogen chloride had ended, the mixture was cooled, the pressure was relieved, the excess hydrofluoric acid was distilled off and the 2,4-difluoro-5-trifluoromethyl-pyrimidine obtained was distilled off with a boiling point of 105° C. at normal pressure. The yield was 204 g (=74% of theory).

The $^1H$ NMR spectrum (200 MHz, $CDCl_3$) showed a characteristic signal at $\delta=9.02$ ppm. The $^{19}F$ NMR spectrum (188 MHz, $CDCl_3$) showed characteristic lines at $\delta=-36.65$ ppm, $-52.85$ ppm and $-62.02$ ppm. The mass spectrum (EI, 70 eV) showed characteristic absorptions at m/z=184 (85%), 165 (80%), 138 (15%), 119 (15%), 93 (55%), 69 (70%) and 31 (100%).

Example 4 (Preparation of 5-trifluoromethyl-uracil)

A solution of 11.3 g of potassium fluoride in 100 ml of water was added to 18.4 g of 2,4-difluoro-5-trifluoromethyl-pyrimidine and the mixture was stirred for 15 hours at 25° to 30° C. It was then briefly boiled and filtered hot and the filtrate was concentrated and left to cool, 5-trifluoromethyl-uracil crystallising out with a melting point of 249° to 251° C. The yield was 16.4 g (=91% of theory).

The following characteristic data were obtained by NMR spectroscopy: $^1$H NMR (200 MHz, dimethyl sulphoxide): δ=11.5 and 8.0; $^{19}$F NMR (188 MHz, dimethyl sulphoxide): δ=−61.1.

Example 5 ( Preparation of 2,4-difluoro-5-trifluoromethyl-pyrimidine )

500 g of 2,4-dichloro-5-trichloromethyl-pyrimidine and 600 ml of anhydrous hydrofluoric acid were placed in a stainless steel stirred autoclave at 0° C. The apparatus was sealed, a pressure of 10 bar of nitrogen was applied and the mixture was heated to 142° C. The pressure of the hydrogen chloride formed was relieved continuously via a condenser. The reaction time was 4 hours. The mixture was then cooled, the pressure was relieved and firstly the excess hydrofluoric acid and then the product were separated off by distillation to give 311 g (=90% of theory) of 2,4-difluoro-5-trifluoromethyl-pyrimidine with a boiling point of 105° C. at normal pressure.

Example 6 (Preparation of a mixture of 2,4-dihalogeno-5-trifluoromethyl-pyrimidines)

27 g of 2,4-dichloro-5-trichloromethyl-pyrimidine, 50 g of antimony trifluoride and 5 g of antimony pentachloride were placed in a stirred apparatus and stirred at 150° to 160° C. for 4 hours. The trifluoromethyl-pyrimidines contained in the reaction mixture were separated therefrom by vacuum distillation to give 10 g of a product mixture which, according to $^1$H NMR spectroscopic analysis, consisted of 44% by weight of 2,4-difluoro-5- trifluoro-methyl-pyrimidine, 36% by weight of 2-chloro-4-fluoro-5-trifluoromethyl-pyrimidine and 20% by weight of 2,4-dichloro-5-trifluoromethyl-pyrimidine.

Example 7 (Preparation of 5-trifluoromethyl-uracil)

510 g of potassium fluoride were placed in 4900 ml of water, and 1620 g of 2,4-difluoro-5-trifluoromethyl-pyrimidine were added. The mixture was then stirred for 5 hours at 50° C. The 5-trifluoromethyl-uracil which had crystallised out was then filtered off with suction to give 1442 g (=91% of theory) of product with a melting point of 251° to 252° C.

What is claimed is:

1. A process for the preparation of 5-(trifluoromethyl)uracil, comprising:
    a. chlorinating thymine by reacting thymine with phosphorus oxychloride in the presence of a tertiary amine at 20° to 120° C. to yield 2,4-dichloro-5-methylpyrimidine,
    b. chlorinating 2,4-dichloro-5-methylpyrimidine by reacting 2,4-dichloro-5-methylpyrimidine with elemental chlorine or sulphuryl chloride at temperatures of 180° to 250° C., in the presence of radical-forming agents, without using a solvent, and optionally under UV irradiation to yield 2,4-dichloro-5-trichloromethylpyrimidines,
    c. reacting 2,4-dichloro-5-trichloromethylpyrimidine with a catalytic amount of antimony halides and excess hydrogen fluoride or hydrogen fluoride alone to yield 2,4-fluorinated and/or chlorinated 5-trifluoromethylpyrimidine, and
    d. hydrolyzing the 2,4-fluorinated and/or chlorinated 5-trifluoromethylpyrimidines with excess water and in the presence of a fluoride selected from the group consisting of potassium fluoride and sodium fluoride to yield 5-(trifluoromethyl) uracil.

2. The process of claim 1, in which in step c) the fluorination is carried out at 80° to 180° C. with mixtures of antimony trifluoride and antimony pentachloride.

3. The process of claim 1, in which in step c) the fluorination is carried out at 80° to 180° C. with hydrogen fluoride.

4. The process of claim 1, in which step d) is carried out at 20° to 90° C.

5. The compound 2,4-dichloro-5-trichloromethyl-pyrimidine.

6. The compound 2,4-difluoro-5-trifluoromethyl-pyrimidine.

* * * * *